United States Patent
Sato et al.

(12) 
(10) Patent No.: US 6,414,113 B1
(45) Date of Patent: Jul. 2, 2002

(54) PEPTIDES BINDING TO BONE MARROW STROMAL CELL ANTIGEN

(75) Inventors: Atsushi Sato, Kamakura; Hisato Jingami, Kyoto, both of (JP)

(73) Assignee: Biomolecular Engineering Research Institute, Osaka (JP)

( * ) Notice: Subject to any disclaimer, the term of this patent is extended or adjusted under 35 U.S.C. 154(b) by 0 days.

(21) Appl. No.: 09/300,410

(22) Filed: Apr. 27, 1999

(30) Foreign Application Priority Data

Apr. 28, 1998 (JP) ............................................ 10-118586

(51) Int. Cl.⁷ ............................................... A61K 38/00
(52) U.S. Cl. ..................... 530/326; 530/412; 424/184.1; 514/14; 435/4; 604/5.01
(58) Field of Search ................................. 530/326, 412; 424/184.1; 514/14; 435/4; 604/5.01

(56) References Cited

FOREIGN PATENT DOCUMENTS

WO        94/17184        8/1994

OTHER PUBLICATIONS

Ngo et al. The Protein Folding Problem and Tertiary Structure Prediction, Merz, Editor, Birkhauser Boston pp. 492–495.*

A. Sato et al., "Novel peptide inhibitor of ecto–ADP–ribosyl cyclase of bone marrow stromal cell antigen–1 (BST–1/CD157)", Biochemical Journal, vol. 337, No. 3, pp. 491–496, Feb. 1, 1999.

M. Torti et al., "Cytoskeleton–dependent inhibition of the ADP–ribosyl cyclase activity of CD38 in thrombin–stimulated platelets", FEBS Letters, vol. 431, No. 1, pp. 19–22, Jul. 10, 1998.

Y. Kajimoto et al., "Pancreatic islet cells express BST–1, a CD38–like surface molecule having ADP ribosyl cyclase activity", Biochemical and Biophysical Research Communications, vol. 219, No. 3, pp. 941–946, Feb. 27, 1996.

M. Hara–Yokohama et al., "Ihibition of $NAD^+$ glycohydrolase and ADP–ribosyl cyclase activities of leukocyte cell surface antigen CD38 by gangliosides", The Journal of Biological Chemistry, vol. 271, No. 22, pp. 12951–12955, May 31, 1996.

Y. Okuyama et al., "Human BST–1 expressed on myeloid cells functions as a receptor molecule", Biochemical and Biophysical Research Communications, vol. 228, No. 3, pp. 838–845, Nov. 21, 1996.

* cited by examiner

*Primary Examiner*—Patrick J. Nolan
(74) *Attorney, Agent, or Firm*—Wenderoth, Lind & Ponack, L.L.P.

(57) ABSTRACT

Peptides capable of binding to bone marrow stromal cell antigen-1 (BST-1), and peptides capable of binding to BST-1 and inhibiting ADP-ribosyl cyclase activity and cADP-ribose hydrolase activity thereof are provided. The peptides are useful for treating rheumatoid arthritis and multiple myeloma.

12 Claims, 8 Drawing Sheets

Inhibition of Enzymatic Activities by Peptide SNP-1 lane 1: Culture Supernatant
lane 2: Marker
lane 3: Unbound Fraction
lane 4: Washed Fraction
lane 5: Eluted Fraction

PEPTIDES BINDING TO BONE MARROW STROMAL CELL ANTIGEN

BACKGROUND OF THE INVENTION

1. Field of the Invention

The present invention relates to peptides binding to bone marrow stromal cell antigen-1 (referred to as "BST-1" hereinafter) and peptides that bind to the antigen BST-1 and inhibit ADP-ribosyl cyclase activity of the antigen. The peptides may be used for treating rheumatoid arthritis (sometimes referred to as "RA" hereinafter), multiple myeloma (sometimes referred to as "MM" hereinafter) and the like.

2. Description of the Related Art

Bone marrow stromal cell lines derived from RA patients were reported to have increased proliferation-enhancing activity on DW34 which is mouse stromal cell-dependent pre-B cell, when compared with those from normal volunteer (J. Immunol., 149, 4088–4095, 1992). It was also reported that bone marrow stromal cell lines from RA and MM patients showed increased proliferation-enhancing activity on pre-B cell, and a novel bone marrow stromal cell antigen-1 was successfully isolated based on the assumption that the bone marrow stromal cells from RA and MM patients must contain some proliferation-accelerator (Proc. Natl. Acad. Sci. USA, 91, 5325–5329, 1994).

BST-1 is a glycosyl-phosphatidylinositol (GPI)-anchored membrane protein carrying hydrophobic signal peptide at the C-terminal. BST-1 is considered to function as a signal transmitter (receptor) since intracellular proteins are phosphorylated or dephosphorylated when BST-1 is stimulated by crosslinking with its polyclonal antibodies (Biochem. Biophys. Res. Commun., 228, 838–845, 1996). BST-1 shows 30% homology with human lymphocyte antigen CD38 at the amino acid level, and it is known that BST-1 has cyclic ADP-ribose hydrolase activity as well as ADP-ribosyl cyclase activity like CD38 (FEBS letters, 356, 244, 1994). As well known, the term "ADP" is an abbreviation for adenosine 5'-diphosphate, and the cyclic ADP-ribose is referred to as cADP-ribose hereinafter.

ADP-ribosyl cyclase activity is an enzymatic action which converts nicotinamide adenine dinucleotide (NAD) to cADP-ribose, and the latter is being watched with interest as a second messenger for releasing $Ca^{2+}$ from intra-cellular $Ca^{2+}$ stores with a mechanism different from inositol 1,4,5-triphosphate (IP3) (Science, 253, 1143–1146, 1993). Through cADP-ribose hydrolase activity, cADP-ribose is hydrolized to ADP-ribose.

BST-1 and CD38 have their catalytic regions on the extracellular side, and therefore, it would be an interesting theme to investigate how their extracellular enzymatic activities can perform the $Ca^{2+}$ release from intracellular $Ca^{2+}$ stores, considering that the cADP-ribose can hardly cross the plasma membrane.

It has been shown that arthrosis crevicular fluid of RA patients contains significantly high concentration of soluble BST-1 as compared with that of normal volunteers (Arthritis Rheum., 39, 629–637, 1996), and it is suggested that there may be some relation between ADP-ribosyl cyclase activity of the soluble BST-1 and pathogenesis of rheumatoid arthritis. However, unavailability of an inhibitor specifically inhibiting ADP-ribosyl cyclase activity has hindered researchers from investigating this subject.

SUMMARY OF THE INVENTION

As stated above, precise relationship between BST-1 isolated from stromal cells of RA or MM patients and the pathogenesis has not been established yet. In particular, relation between ADP-ribosyl cyclase activity of BST-1 and the pathogenesis has not been clarified yet. In such a situation, the inventors of the present invention considered that the use of an agent inhibiting such ADP-ribosyl cyclase activity would be effective for elucidating the relation. After extended studies for this purpose, they succeeded in obtaining novel peptides binding to BST-1, and additional novel peptides binding to BST-1 and yet inhibiting ADP-ribosyl cyclase activity thereof. The present invention is based on such findings.

Thus, the invention provides peptides binding to BST-1, in particular, peptides binding to BST-1 and yet inhibiting ADP-ribosyl cyclase activity of BST-1.

DESCRIPTION OF THE PREFERRED EMBODIMENTS

Figure 1:
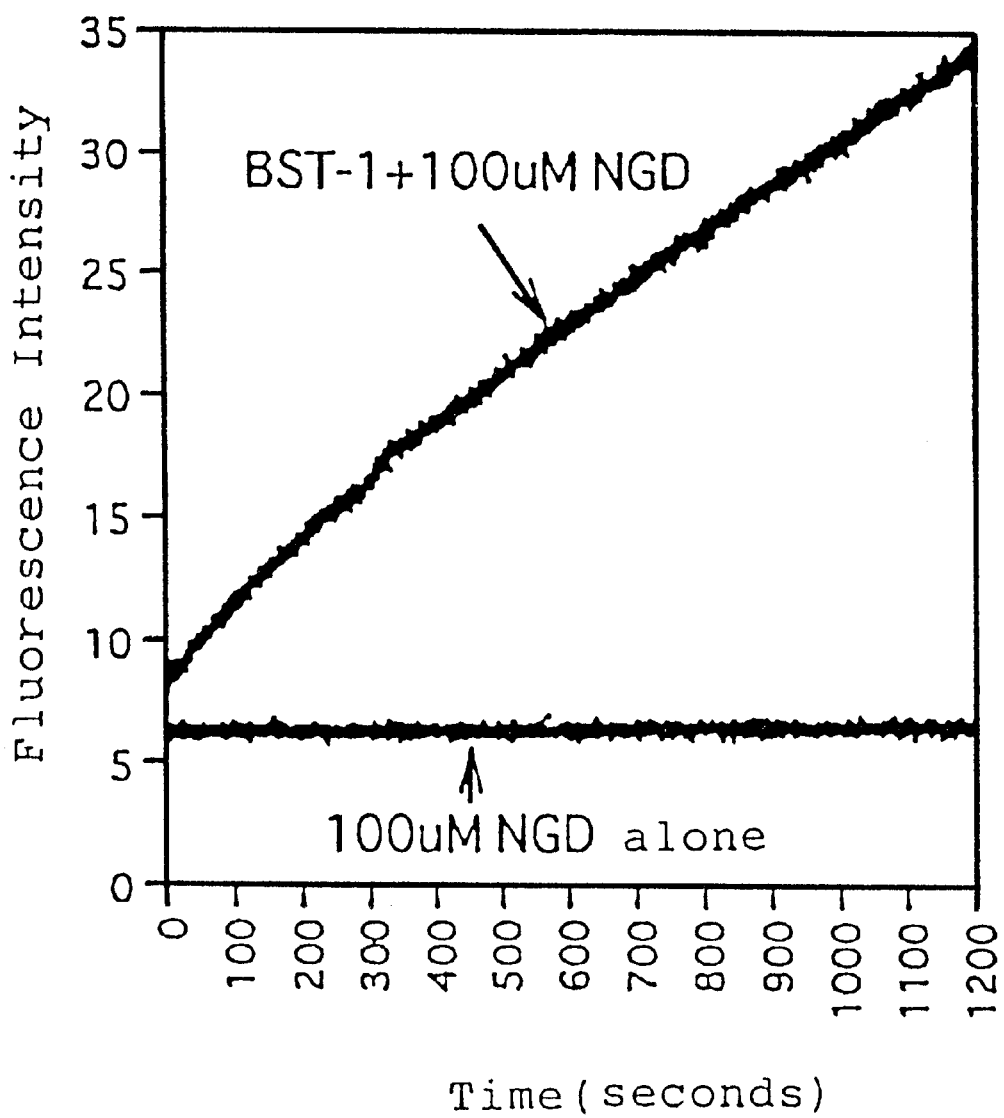
FIG. 1 represents ADP-ribosyl cyclase activity of purified BST-1 when measured using NGD as a substrate. The ordinate represents fluorescence intensity and the abscissa represents time course.

For the purpose of seeking an agent that binds to BST-1, human BST-1 was expressed in insect cells, and highly purified BST-1 was obtained in a large amount. Using purified BST-1, the inventors have selected from a phage display peptide library (Jikken Igaku Experimental Medicine, 11, No. 13, August, 95–100, 1993) two peptides consisting of 15 amino acid residues that bind to BST-1. One of them was identified to inhibit ADP-ribosyl cyclase activity. Details of the procedures are discussed below.

Human BST-1 may be prepared by, for example, recombinant DNA technology. Host cells for the expression may be selected from *E. coli*, yeast, insect, and animal cells. When insect cells are used, cDNA encoding human BST-1 (Kaisho T. et al, Proc. Natl. Acad. Sci. USA, 91, 5325–5329, 1994) is inserted downstream of a promoter which functions in insect cells, for instance, polyhedrine promoter, in conventional manner (King and Possee, The baculovirus expression system, Chapman & Hall, 1992). Purification of expressed products may be accomplished by salting out, ion-chromatography, centrifugation, and the like.

For obtaining peptides that bind to human BST-1, a peptide library method may be conveniently used as described below.

Random peptide phage library may be constructed by binding synthetic genes having random sequences to, for instance, coat protein genes (e.g. gene III or IIIV) of M13 phage. For this purpose, the method described in Science, 249, 386, 1990, or Proc. Natl. Acad. Sci., USA, 87, 6378, 1990, may be used. Size of the synthetic gene to be inserted is not limitative so far as the expressed peptide is stable. However, the gene having preferred size will be the one encoding from six (6) to fifteen (15) amino acid residues so that the resulting library may cover as many random sequences as possible and can bind to the target molecule, BST-1. Selection of phage capable of binding to BST-1 is accomplished by immobilizing purified BST-1 on a column or plate, directly or via a linker such as antibodies, contacting the library with the immobilized BST-1, and then washing out unbound phage. After washing, bound phage are eluted with acids, neutralized, and amplified by infecting *E. coli* cells. This procedure is repeated for three or four rounds to concentrate phage having affinity to BST-1. In order to obtain a single uniform phage, the concentrated phage are infected to *E. coli* cells, and a single colony is allowed to form on an agar plate containing antibiotics. The colony is cultured in a liquid medium, and the phage in supernatant is concentrated by precipitation with polyethylene glycol. Sequencing of the phage DNA reveals the amino acid sequence of the peptide bound to BST-1.

The peptide library containing random amino acid sequences may also be prepared by chemical synthesis by means of a method employing beads (Nature, 354, 82, 1991), liquid phase focusing (Nature, 354, 84, 1991) and micro plate method, and the like.

Large-scale production of the desired peptide may be carried out by chemical synthesis or recombinant DNA technology using *E. coli*, yeast, insect, or animal cells as a host. Conventional peptide synthesis may be used for the former, and solid phase synthesis is preferred. In this method, preparation of variant peptides in which one or more amino acid residues are altered may be readily accomplished (Saibo Kogaku (cell technology), extra number, Experimental protocol for anti-peptide antibody, p26–46, Shu-jun sha, 1994). As for the latter, it is an established technique that the DNA sequence is determined according to the amino acid sequence of the peptide bound to BST-1 on the basis of codon usage, and a DNA prepared according to the DNA sequence determined is incorporated into a host cell (Maniatis et al; Molecular Cloning, Appendix D1, Cold Spring Habor Laboratory, 1989). Amino acid residue(s) in the sequence can be substituted with other amino acid residue(s) by incorporation of mutation into the DNA sequence.

When the peptide is expressed in *E. coli* cells, it is preferred that the resulting DNA is linked with a promoter sequence, such as tryptophan synthetase operon (Trp) promoter or lactose operon (lac) promoter, a ribosome-binding sequence, such as Shine-Dalgarno sequence, and a transcription terminator recognition site, is added thereto. The resulting expression vector may be inserted into *E. coli* cells according to the methods described in the afore-mentioned Molecular Cloning. Expressed products may be purified by, for example, various kinds of chromatography.

The fact that the peptide thus obtained inhibits ADP-ribosyl cyclase activity of BST-1 may be identified by comparing the ADP-ribosyl cyclase activity when measured in the absence of the peptide with the activity in the presence of the peptide. As previously mentioned, NAD is converted to cADP-ribose by ADP-ribosyl cyclase activity of BST-1, and therefore, the activity may be measured by allowing to react NAD with BST-1 and then quantitatively determining NAD and cADP-ribose after separation of them by anion-exchange chromatography (FEBS letters, 356, 244, 1994). Alternatively, nicotinamide guanine dinucleotide (NGD) may be used as a substrate instead of NAD, which is converted to cyclic guanosine-5'-diphosphate-ribose cGDP-ribose that can be fluorimetrically measured with an excitation wavelength of 300 nm and an emission wavelength of 410 nm, whereby the velocity of the formation of cGDP-ribose reflects ADP-ribosyl cyclase activity (J. Biol. Chem., 48, 30260, 1994).

The present invention has enabled those skilled in the art to obtain peptides that bind to BST-1, and additional peptides that bind to BST-1 and yet specifically inhibit ADP-ribosyl cyclase activity thereof. The peptides may be used for treating rheumatoid arthritis and multiple myeloma. In addition, the peptides may be immobilized on a carrier and used as a component of a medical extraperfusion apparatus for removing BST-1 from body fluid.

In more detail, the first object of the present invention is to provide peptides capable of binding to BST-1, which comprise an amino acid sequence (1) depicted in SEQ ID NO: 1 or an amino acid sequence (2) obtained by making deletion, substitution, or insertion of one or more amino acid residues to the amino acid sequence (1). As preferred embodiments are provided peptides having the amino acid sequence (2) which contains deletion, substitution, or insertion of amino acid residue(s) at the positions of 1, 3, 6, 13, and/or 14 of the amino acid sequence of SEQ ID NO: 1.

The second object of the invention is to provide peptides capable of binding to BST-1, which comprise an amino acid sequence (3) depicted in SEQ ID NO: 2 or an amino acid sequence (4) obtained by making deletion, substitution, or insertion of one or more amino acid residues to the amino acid sequence (3).

The third object of the invention is to provide peptides which bind to BST-1 and yet specifically inhibit ADP-ribosyl cyclase activity thereof.

The fourth object of the invention is to provide peptides which bind to BST-1 and yet specifically inhibit cADP-ribose hydrolase activity thereof.

The fifth embodiment of the invention is to provide a pharmaceutical formulation comprising as an essential component at least one of the peptides defined in the preceding objects.

The sixth object of the invention is to provide a diagnostic agent for detecting BST-1, which comprises as an essential component at least one of the peptides defined in the preceding objects.

The seventh object of the invention is to provide an adsorbing agent comprising at least one of the peptides defined in the preceding objects, said peptide(s) being immobilized on a carrier.

The eighth object of the invention is to provide a method for purification of BST-1 using the adsorbing agent defined above.

The ninth object of the invention is to provide a medical extraperfusion apparatus which contains as one of the components at least one of the peptides defined in the preceding objects, said peptides capable of inhibiting enzymatic activities of BST-1.

The tenth object of the invention is to provide a method of screening a substance capable of interacting with BST-1, which employs at least one of the peptides defined in the preceding objects.

Other objects of the present invention will be apparent to those skilled in the art from the disclosure of the specification and the drawings.

In the accompanying drawings:

FIG. 1 represents ADP-ribosyl cyclase activity of purified BST-1 when measured using NGD as a substrate. The ordinate represents fluorescence intensity and the abscissa represents time course. Purified BST-1 (5 μg/ml) was mixed with 100 μM NGD, allowed to react for 20 minutes at 25° C., and fluorescence intensity was measured with an excitation wavelength of 300 nm and an emission wavelength of 410 nm. When only the substrate (100 μM NGD) was allowed to react, fluorescence did not increase due to no formation of cGDP-ribose. However, when BST-1 was added to the substrate, fluorescence was linearly increased, which confirmed the enzymatic activity of BST-1.

Figure 2:
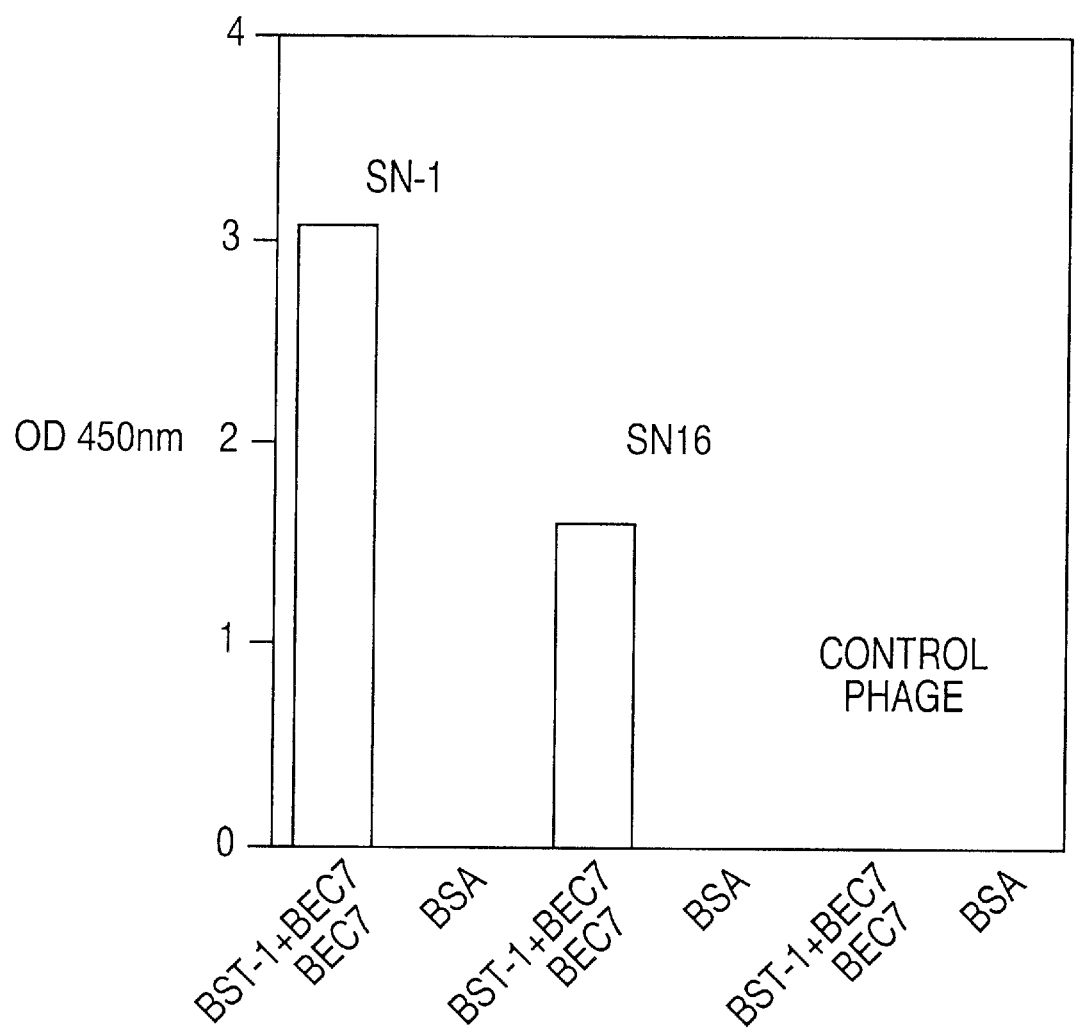
FIG. 2 shows ELISA analysis of phage obtained by screening of phage display peptide library with BST-1. The ordinate represents absorbance at 450 nm and the abscissa represents phage's names.

FIG. 2 shows ELISA analysis of phage obtained by screening of phage display peptide library with BST-1. The ordinate represents absorbance at 450 nm and the abscissa represents phage's names: SN-1 is a phage expressing the peptide defined by SEQ ID NO: 1; SN-16 is a phage expressing the peptide defined by SEQ ID NO: 2; Control is a negative control phage having unrelated sequence. SN-1 and SN-16 reacted with the well on which BST-1 was immobilized via antibody BEC 7 (Okuyama Y. et al; Biochem. Biophys. Commun. 228, 838–845, 1996), while they did not react with the well on which only BEC 7, BST-1, or bovine serum albumin (BSA) was immobilized. This confirmed that they specifically bind to BST-1.

Figure 3:
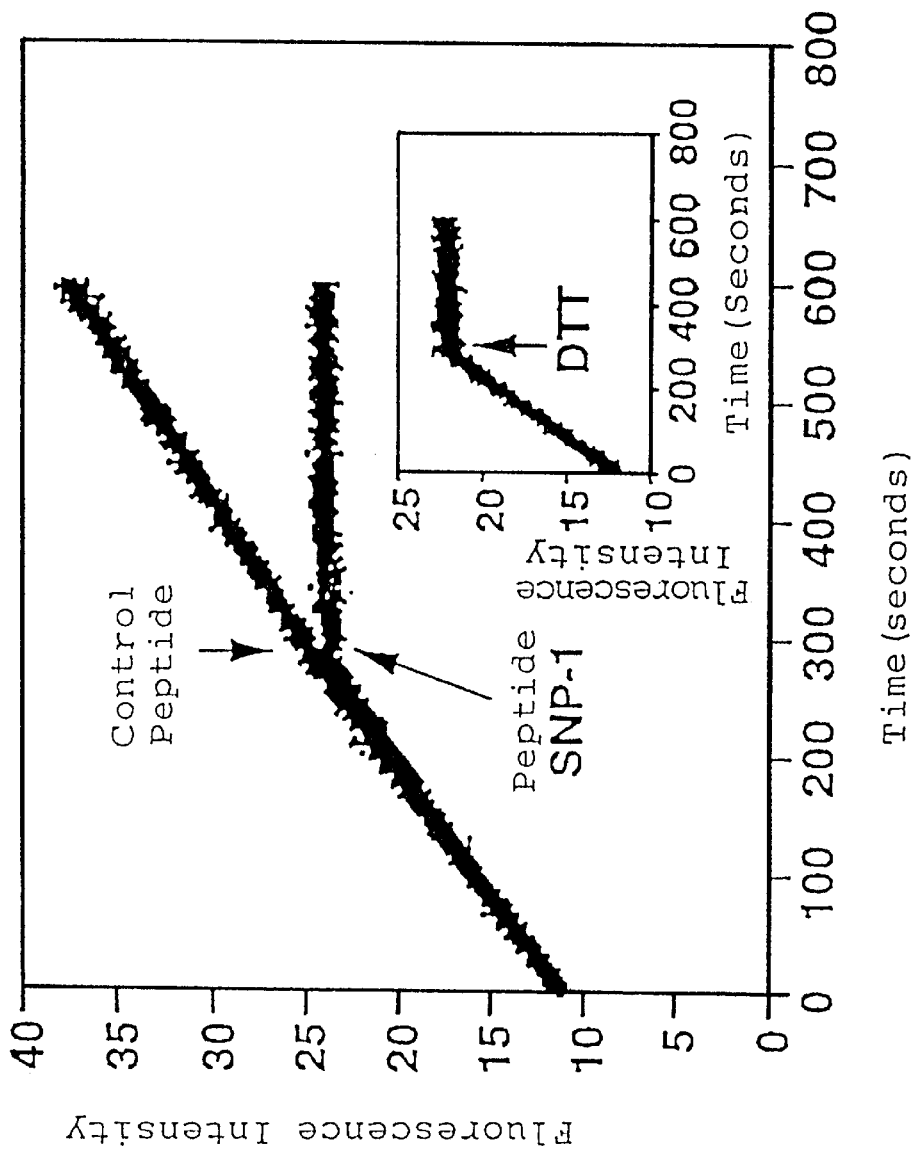
FIG. 3 shows an inhibition of ADP-ribosyl cyclase activity of BST-1 by synthetic peptide SNP-1. The abscissa is time course and the ordinate is fluorescence intensity.

FIG. 3 shows an inhibition of ADP-ribosyl cyclase activity of BST-1 by synthetic peptide SNP-1. The abscissa is time course and the ordinate is fluorescence intensity. Purified BST-1 (4 μg/ml) was mixed with NGD (300 μM), and the mixture was allowed to react at 25° C. for 300 seconds, and then the synthetic peptide SNP-1 was added thereto at the concentration of 20 μM. Upon addition of the peptide, increase of fluorescence intensity was stopped, which meant complete inhibition of ADP-ribosyl cyclase activity by the peptide. On the other hand, addition of negative control peptide at the concentration of 20 μM did not give any influence on the increase of fluorescence intensity. The inset shows a complete disappearance of ADP-ribosyl cyclase activity by the addition of a reducing agent DTT at the concentration of 10 mM.

Figure 4:
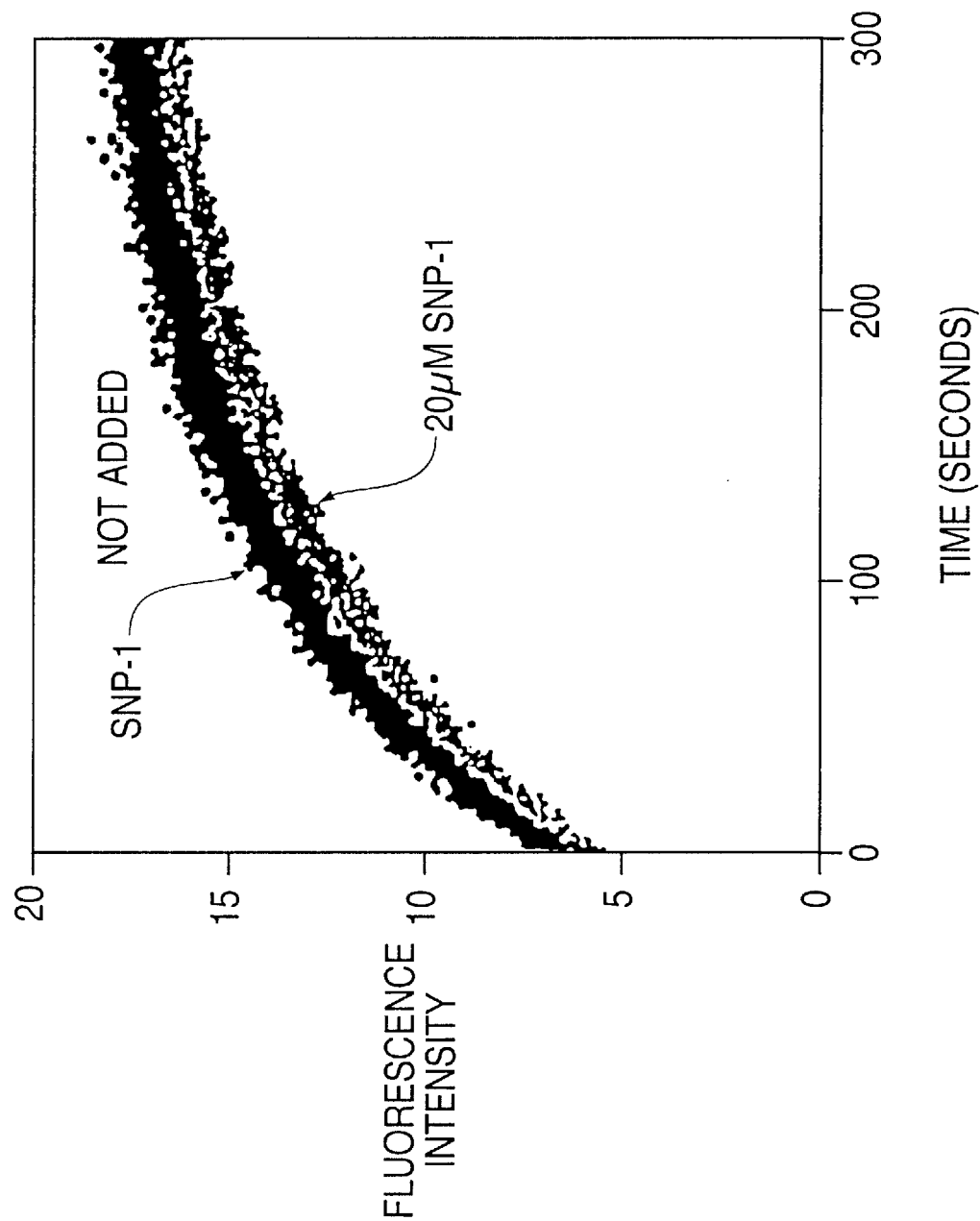
FIG. 4 shows that the synthetic peptide SNP-1 did not inhibit ADP-ribosyl cyclase activity of CD38. The abscissa is time course and the ordinate is fluorescence intensity.

FIG. 4 shows that the synthetic peptide SNP-1 did not inhibit ADP-ribosyl cyclase activity of CD38. The abscissa is time course and the ordinate is fluorescence intensity. Purified CD38 (200 ng/ml) was mixed with NGD (2 μM), and allowed to react at 25° C. for 300 seconds. Addition of the synthetic peptide SNP-1 at the concentration of 20 μM did not give any influence on the increase of fluorescence intensity. Thus, SNP-1 did not inhibit the activity of CD38.

Figure 5:
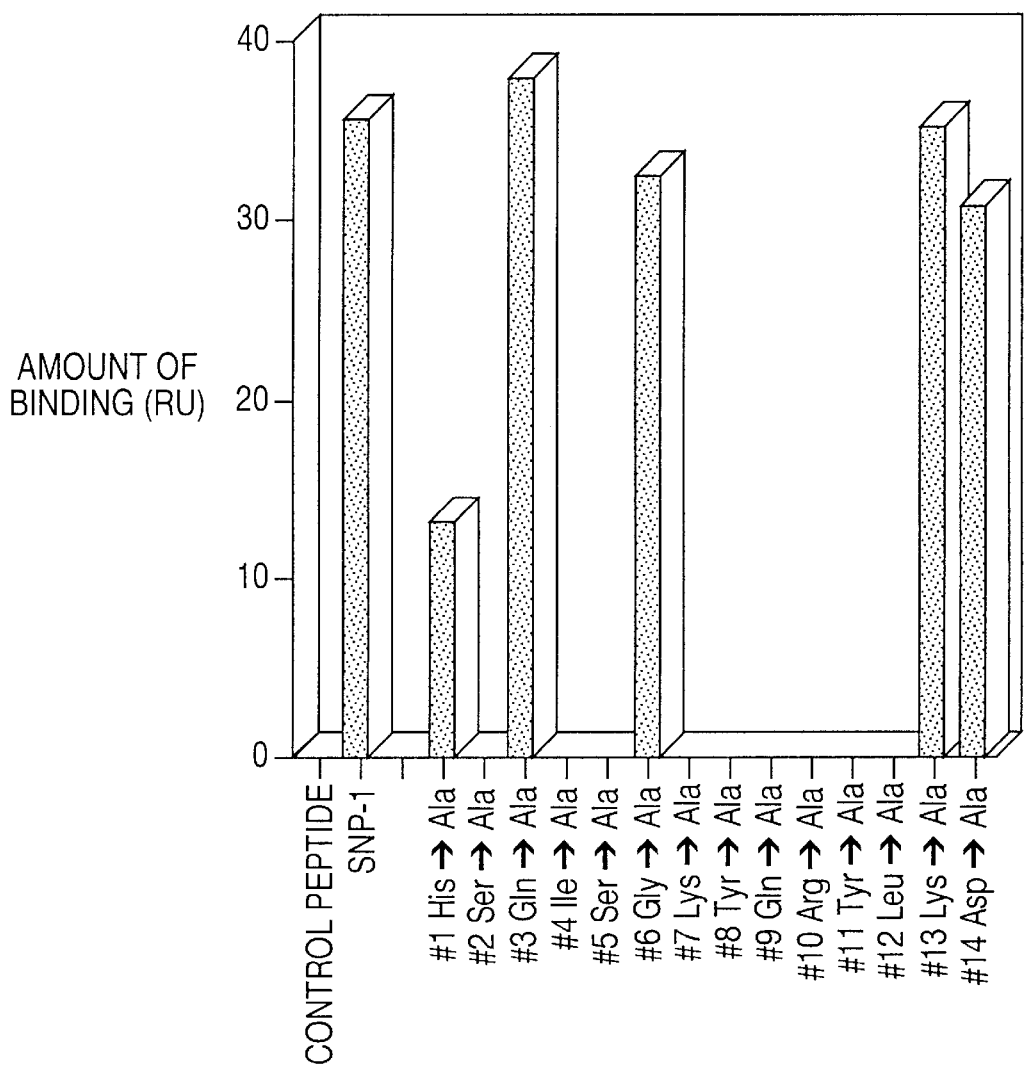
FIG. 5 shows binding of BST-1 with variants of SNP-1. The abscissa shows variants of SNP-1, wherein one of the amino acid residues of SNP-1 is replaced by Ala, and the ordinate shows a magnitude of binding (RU) when measured in Biacore system.

FIG. 5 shows binding of BST-1 with variants of SNP-1. The abscissa shows variants of SNP-1, wherein one of the amino acid residues of SNP-1 is replaced by Ala, and the ordinate shows a magnitude of binding (RU) when measured in Biacore system. The variants #1, #3, #6, #13, and #14 retained binding ability, while the other variants lost the binding ability. The control peptide was the one prepared in Example 2.

Figure 6:
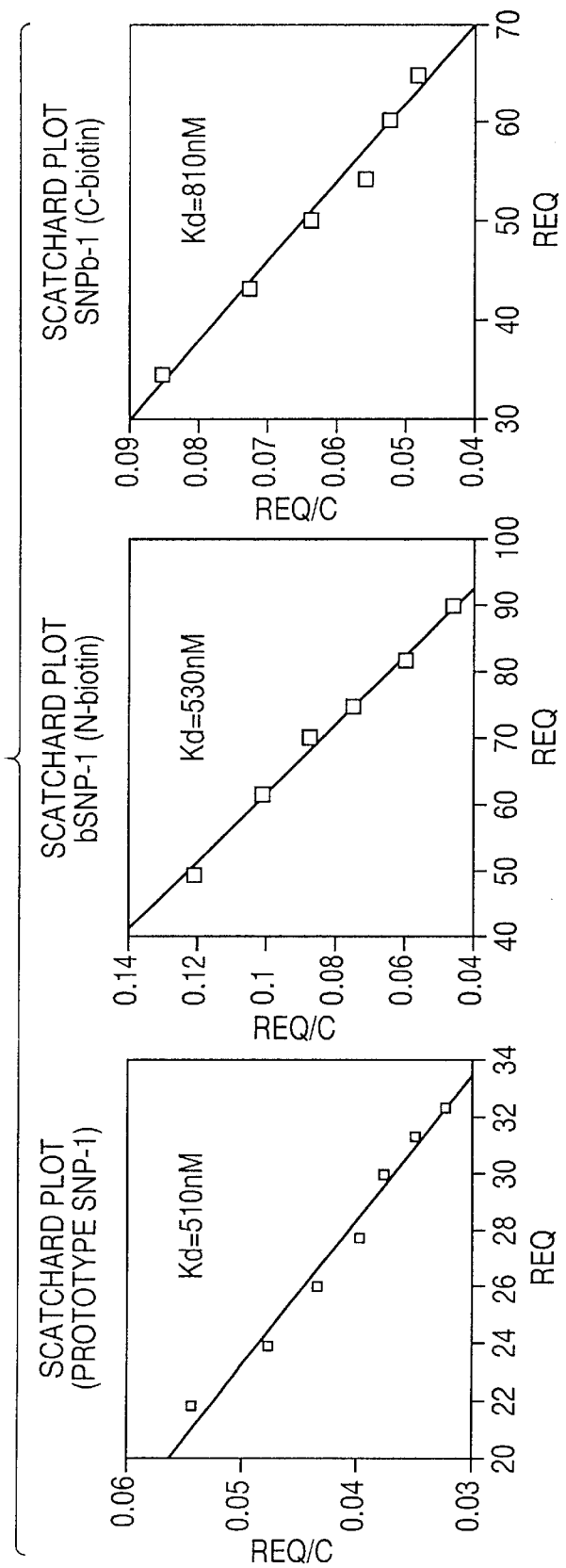
FIG. 6 shows binding of BST-1 with SNP-1 which was modified with biotin at the N- or C-terminal. The graphs show Scatchard plot of prototype (original) SNP-1 (a), bSNP-1 (b) which has biotin bound at the N-terminal, and SNPb-1 (c) which has biotin bound at the C-terminal.

FIG. 6 shows binding of BST-1 with SNP-1 which was modified with biotin at the N- or C-terminal. The graphs show Scatchard plot of prototype (original) SNP-1 (a), bSNP-1 (b) which has biotin bound at the N-terminal, and SNPb-1 (c) which has biotin bound at the C-terminal. The slope of the linear lines determined the dissociation constants of SNP-1, bSNP-1, and SNPb-1 as 510 nM, 530 nM, and 810 nM, respectively. Absence of remarkable difference among them in terms of their dissociation constants shows that modification of N- or C-terminal with biotin did not result in the loss of the binding ability of SNP-1. In the drawing, Req means equilibrium binding value expressed by resonance unit (RU), and Req/C represents the value obtained by dividing the equilibrium binding value with the peptide concentration.

Figure 7:
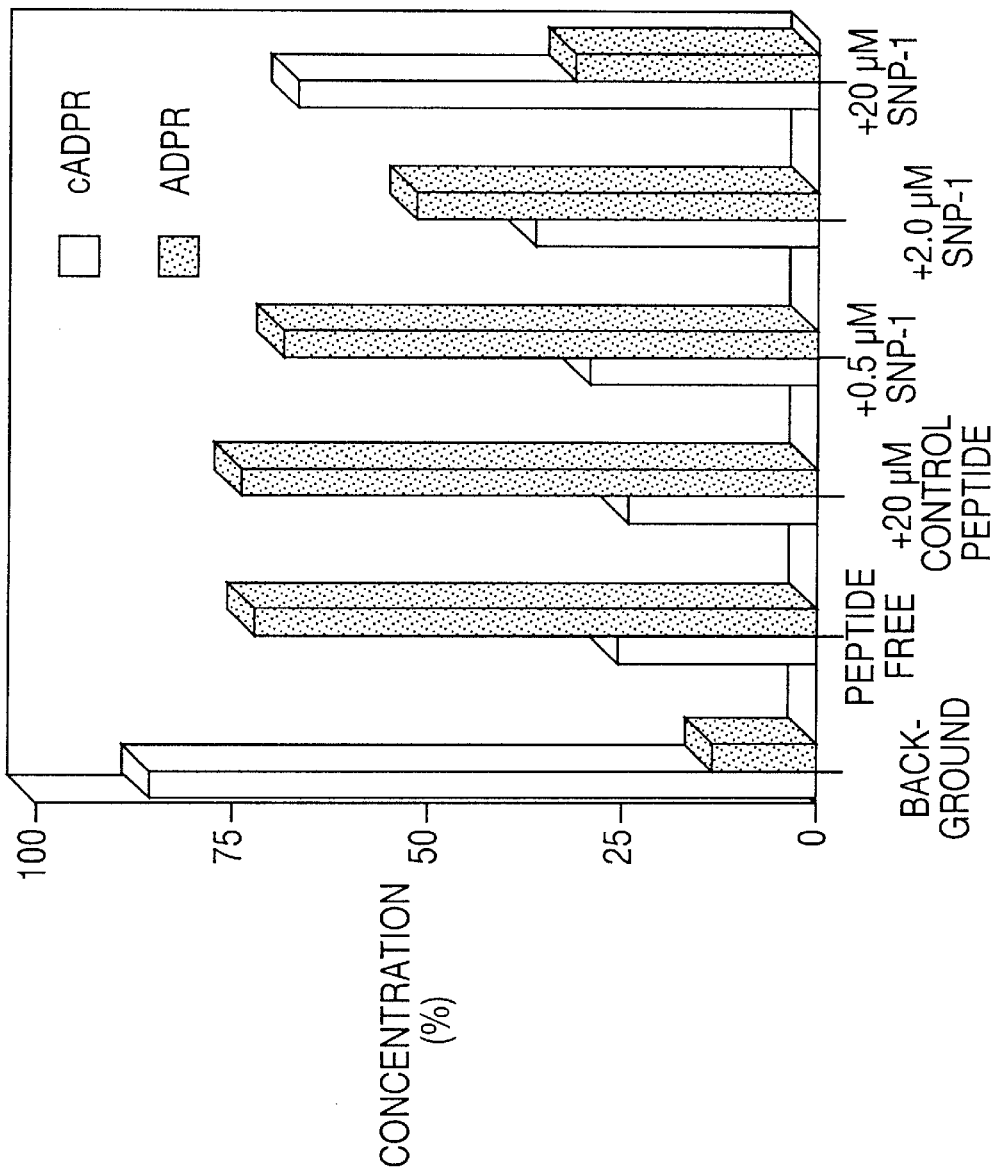
FIG. 7 shows an inhibition of cADP-ribose hydrolase activity of BST-1 by SNP-1.

FIG. 7 shows an inhibition of cADP-ribose hydrolase activity of BST-1 by SNP-1. cADP-ribose hydrolase activity of BST-1 converts cADP-ribose to ADP-ribose. After reaction of BST-1 and cADP-ribose, two riboses were separated by HPLC, and the formation of ADP-ribose was determined based on the peak area. The total peak area of cADP-ribose and ADP-ribose corresponded to 100%. SNP-1 inhibited the formation of ADP-ribose dose-dependently, while a control peptide did not give any influence on the formation of ADP-ribose at the concentration of 20 μM. "Background" in the figure represents the results of the reaction involving only the substrate, cADP-ribose, and reflects spontaneous hydrolysis. "Peptide free" means the enzymatic reaction carried out without the peptide.

Figure 8:
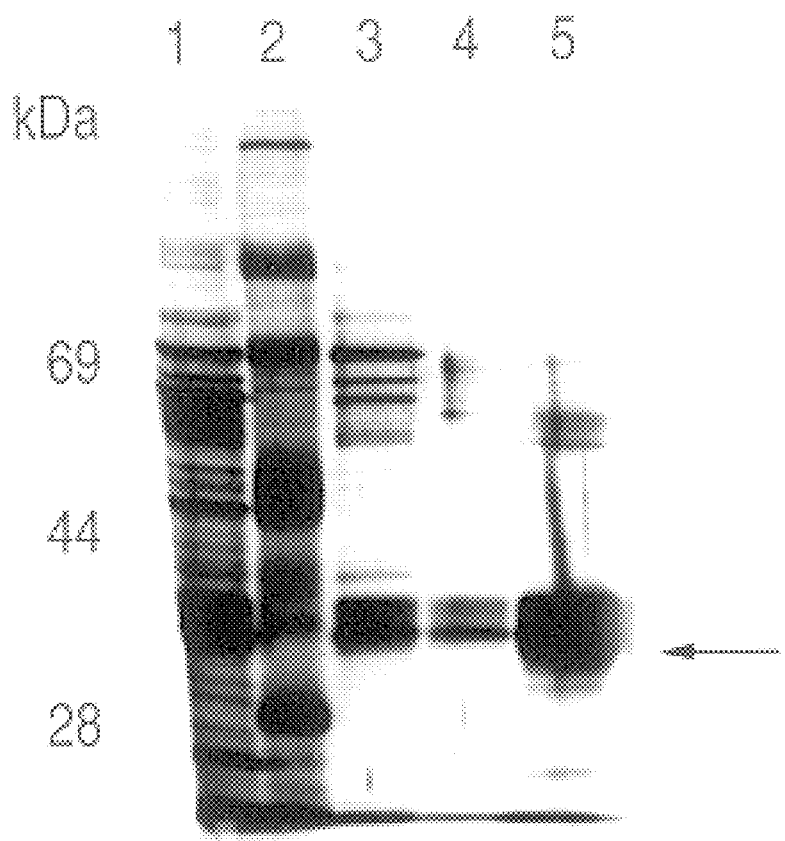
FIG. 8 is an electrophoretic photograph which shows the results of purification of BST-1 using SNPb-1 affinity chromatography.

FIG. 8 is an electrophoretic photograph which shows the results of purification of BST-1 using SNPb-1 affinity chromatography. Eluted fractions, each 20 μl, were analyzed with SDS-PAGE (7.5%), and BST-1 was detected by means of silver staining. Various proteins were detected in non-purified culture supernatant, while the fractions eluted by SNPb-1 affinity chromatography contained almost completely purified BST-1.

The following detailed Examples and Reference Examples are presented by way of illustration of certain specific embodiments of the invention. The Examples are representative only and should not be construed as limiting in any respect.

Reference Example 1

Expression and Purification of BST-1

As previously mentioned, BST-1 is a GPI-anchored membrane protein (Proc. Natl. Acad. Sci. USA, 91, 5325, 1994). In order to produce a large amount of soluble BST-1 using insect cells, BST-1 cDNA in which the 298th codon (ACA) existing just before the hydrophobic domain at the C-terminal has been substituted by the termination codon (TGA) was inserted at SmaI, XbaI site of an expression plasmid for insect cells, pVL1393 (PharMingen). In accordance with the conventional manner (King and Possee; The baculovirus expression system, Chapman & Hall, 1992), insect cells Sf9 (Funakoshi) were transfected with the resulting plasmid to obtain the recombinant virus. The virus was infected to insect cells, High five (Invitrogen), and the cells were cultured at 27° C. for three days in accordance with the conventional manner (King and Possee; The baculovirus expression system, Chapman & Hall, 1992). Soluble BST-1 secreted into the culture medium was identified by western blotting. The infected insect cells were cultured in a large scale, and BST-1 was purified up to 95% or more by cation-exchange chromatography and dye ligand Blue chromatography. The purified protein was confirmed to have ADP-ribosyl cyclase activity by means of the NGD method mentioned above. See FIG. 1 of the accompanying drawings.

Reference Example 2

Selection of Phage Binding to BST-1

Phage library having random sequences consisting of 15 amino acid residues was prepared using the method described in Biochemistry, 35, 10441, 1996. A monoclonal antibody to BST-1, BEC7 (Okuyama Y. et al; Biochem. Biophys. Res. Commun. 228, 838 –845, 1996), was diluted with 10 mM phosphate buffer, pH 7.0, and coated on 96-well microtiter wells at 40° C. overnight at the ratio of 3 μg/well. To the microtiter wells was added purified BST-1 after dilution with 10 mM phosphate buffer, pH 7.0, at the ratio of 5 μg/well, thereby BST-1 was immobilized on the wells via the antibody. Each well was blocked with 10 mM phosphate buffer, pH 7.0, containing 1% bovine serum albumin at room temperature for one hour. Subsequently, about $10^{12}$ phage library was added to 100 μl of a buffer (10 mM phosphate buffer, pH 7.0, containing 1% bovine serum albumin, 0.05% Tween 20) and the mixture was allowed to react with BST-1 immobilized on the wells at room temperature for one hour. The wells were washed with a washing buffer (10 mM phosphate buffer, pH 7.0, and 0.05% Tween 20) ten times so as to remove unbound phage. Phage bound to BST-1 were eluted out with glycine buffer, pH 2.2, and neutralized with 1M Tris-HCl, pH 9.5. The phage were infected to *E.coli* K91 Kan (obtained from Dr. G. P. Smith of Missouri University), and the infected cells were cultured in LB medium containing tetracycline to amplify the phage. The phage in the supernatant were concentrated by polyethylene glycol precipitation, and the concentrated phage were used in the second round. This procedure was repeated three times in total to select phage binding to BST-1.

Reference Example 3

Selection of Phage Binding to BST-1 by ELISA

The phage selected in Reference Example 2 was infected again to *E. coli* cells K91 Kan, and the cells were cultured on LB agar plate containing tetracycline to form a single colony. The colony was cultured overnight in LB medium containing tetracycline, and the supernatant including the phage was subjected to polyethylene glycol precipitation for the purification of the phage next day. The phage were added to a 96-well microtiter plate, on which BST-1 had been immobilized in advance (see Reference Example 2), at the ratio of about $10^{10}$ phage/well, and allowed to react at room temperature for one hour. After washing four times with a washing buffer (10 mM phosphate buffer, pH 7.0, and 0.05% Tween 20), BST-1 on the well was allowed to react with M13 phage antibody (Pharmacia) labeled with horseradish peroxidase (5000 times diluted) at room temperature for 30 minutes. After washing four times, the substrate, 3,3',5,5'-tetramethyl benzidine, was added for developing color, and the reaction was quenched by the addition of 1M $H_2SO_4$. Absorbance at 450 nm was measured using a microplate reader. The results are shown in FIG. 2.

Reference Example 4

Determination of the Nucleotide Sequence

The nucleotide sequences of the clones that bound to BST-1 in Reference Example 3 were determined. First, phage were subjected to deproteinization by treating them with phenol and chloroform, and the DNA was precipitated by ethanol and used as a template for nucleotide sequencing. A primer was established on the basis of the nucleotide sequence of the vector used, Fuse 5 vector (Smith G. P. and Scott J. K.; Methods Enzymol. 217, 228–257, 1993), and the nucleotide sequences of the clones were determined by using the ABI PRISM dye termination cycle sequencing ready reaction kit (Applied Biosystems). The nucleotide sequences of two clones were thus determined (SN-1: SEQ ID NO: 1, SN-16: SEQ ID NO: 2).

Example 1

Peptide Synthesis

Two peptides, each consisting of 15 amino acid residues, were synthesized by an automated peptide synthesizer on the basis of the amino acid sequences depicted in SEQ ID NOs: 1 and 2 which were deduced from the nucleotide sequences determined. The synthetic peptides having the sequences depicted in SEQ ID NOs:1 and 2 were designated as SNP-1 and SNP-16 respectively. The peptides were found to have purity of 95% or more by means of reverse HPLC.

Example 2

Inhibition of ADP-ribosyl Cyclase Activity of BST-1 by Synthetic Peptides

Inhibition of ADP-ribosyl cyclase activity of BST-1 by synthetic peptides was tested by means of the NGD method previously mentioned. BST-1 at the concentration of 4 μg/ml was allowed to react with the substrate NGD at the concentration of 300 μM at 25° C. for 300 seconds, which confirmed linearly increased fluorescence intensity. After 300 seconds, 20 μM of synthetic peptide SNP-1 was added to the reaction system. As a control, the same amount of a peptide encoding the sequence reverse to the sequence of SNP-1 was used. The addition of the control peptide did not show any inhibition on the activity, while SNP-1 stopped the increase of fluorescence intensity, which confirmed complete inhibition of ADP-ribosyl cyclase activity of BST-1. The results are shown in FIG. 3.

Example 3

Inhibition of ADP-ribosyl Cyclase Activity of CD38 by Synthetic Peptides

It is known that human CD38, like BST-1, has ADP-ribosyl cyclase activity. It was therefore tested whether the synthetic peptides could inhibit ADP-ribosyl cyclase activity of CD38 or not. Thus, to a soluble CD38 at the concentration of 200 ng/ml was added the substrate NGD at a final concentration of 2 μM, and the mixture was allowed to react at 25° C. for 300 seconds, whereby fluorescence intensity was confirmed to increase. Addition of 20 μM of SNP-1 to the reaction system did not inhibit the reaction, which showed that SNP-1 uniquely inhibits ADP-ribosyl cyclase activity of BST-1. FIG. 4 shows the test results.

Example 4

Binding of SNP-1 Variants to BST-1

For the purpose of identifying amino acid residues responsible for the binding of SNP-1 to BST-1, fourteen peptides which are different from SNP-1 only in that they contain Ala in place of one of the original amino acid residues of SNP-1 were chemically synthesized and given the numbers sequentially selected from #1 to #14. For instance, the variant which contains Ala substituted for the first amino acid residue at the N-terminal of SNP-1 was named #1, and the variant which contains Ala substituted for the penultimate amino acid residue was named #14. Fourteen peptides thus prepared were tested for the binding ability to BST-1.

BST-1 was immobilized at 2800 resonance unit (RU) on the sensor chip CM5 of a bio-sensor for analyzing protein interactions, BIACORE (Biacore K.K.), by means of an amine coupling method. The synthetic peptides were passed through the sensor chip at the flow rate of 40 µl/min at the concentration of 500 nM. The amounts (RU) of the peptides bound to BST-1 are shown in FIG. 5. The peptides other than #1, #3, #6, #13, and #14 have lost the binding ability, which shows that the amino acid residues other than positions 1, 3, 6, 13, and 14 are important for the binding. On the other hand, the peptides #1, #3, #6, #13, and #14 have retained the binding ability, which shows that the mutations at the positions 1, 3, 6, 13, and 14 of SNP-1 would not change the binding ability to BST-1.

Example 5

Binding of SNP-1 Derivatives to BST-1

Binding ability to BST-1 of SNP-1 derivative that contains biotinylated N-terminal or C-terminal was compared with that of the prototype SNP-1. The biotinylated SNP-1 was prepared by binding the amino group of N-terminal of SNP-1 with Sulfo-NHS-LC-Biotin (PIERCE) and purifying the product using reverse HPLC. The resultant derivative, having more than 95% purity, was named bSNP-1. In order to biotinylate at the C-terminal, SNP-1 having additional amino acid residue Lys at the C-terminal was chemically synthesized, and biotin was bound to the amino group of the Lys residue. The SNP-1 derivative was purified by reverse HPLC and confirmed to have more than 95% purity. The derivative was named SNPb-1.

BST-1 was immobilized at 2800 resonance unit (RU) on the sensor chip CM5 of a bio-sensor for analyzing protein interactions, BIACORE (Biacore K.K.), by means of an amine coupling method. The synthetic peptides were passed through the sensor chip at the flow rate of 40 µl/min at the concentration of from 400 nM to 2000 nM. Equilibrium binding value was obtained for each concentration. Based on the equilibrium binding values, dissociation constants were calculated by means of Scatchard plot method (Hulme E. C.; Receptor-binding studies, a brief outline, in Receptor Biochemistry: A Practical Approach, 303–315, IRL press, 1990). The control peptide described in Example 2 was used as a negative control and showed no binding ability. The test results are shown in FIG. 6. The dissociation constants (Kd) for the prototype SNP-1, bSNP-1, and SNPb-1, which were determined on the basis of the slope of the linear line, were 510 nM, 530 nM and 810 nM respectively. Similarity of the dissociation constants between SNP-1, bSNP-1, and SNPb-1 shows that the binding ability of SNP-1 to BST-1 is not affected by biotin-modification at the N- or C-terminal.

Example 6

Inhibition of cADP-ribose Hydrolase Activity by the Synthetic Peptides

BST-1 has a cADP-ribose hydrolase activity that hydrolytically converts cADP-ribose to ADP-ribose, as well as the ADP-ribosyl cyclase activity. Accordingly, it was investigated whether or not SNP-1 can also inhibit the cADP-ribose hydrolase activity of BST-1. The hydrolase activity was determined according to the method described in FEBS letters, 356, 244, 1994. Thus, BST-1 at the concentration of 50 µg/ml was mixed with the substrate cADP-ribose at the concentration of 20 µM and allowed to react at 37° C. for four hours. After the reaction, hydrolyzed product, ADP-ribose, was separated by HPLC and the rate of ADP-ribose formation was determined on the basis of the peak area. The total peak area of cADP-ribose and ADP-ribose corresponds 100%. To the reaction system was added SNP-1 at the concentration of 0.5 µM, 2.0 µM, or 20 µM to investigate the inhibition activity. As a control, 20 µM of the control peptide described in Example 2 was used. The test results are shown in FIG. 7, which reveals that SNP-1 inhibits cADP-ribose hydrolase activity dose-dependently, while the control peptide does not inhibit the activity at all at the concentration of 20 µM.

Example 7

Purification of BST-1 by the Use of Biotinylated Peptides

BST-1 was purified by affinity chromatography which takes advantage of the binding between BST-1 and SNP-1 derivative which contains biotinylated C-terminal, i.e., SNPb-1. Thus, an affinity column was prepared by binding $1 \times 10^{-7}$ mol of SNPb-1, which was synthesized according to Example 5, to 1 ml of ultra avidin-agarose gel in a 20 mM MES buffer solution, pH 6.0.

Fifty ml of culture supernatant containing expressed and secreted BST-1 was diluted fivefold with a 20 mM acetate buffer solution, pH 5.0, and partially purified with a cation-exchange chromatography, followed by desalting by means of dialysis against a 20 mM MES buffer solution, pH 6.0. Desalted BST-1 was charged into the afore-mentioned affinity chromatography column and eluted out using 0.5 ml of a 20 mM MES buffer (pH 6.0) containing 1.0 M NaCl, to obtain purified BST-1.

Preparation

Synthetic peptide SNP-1 was mixed with a carrier therefor and encapsulated by conventional manner to obtain capsules for treating rheumatoid arthritis.

What is claimed is:

1. A peptide which binds to bone marrow stromal cell antigen-1, said peptide comprising an amino acid sequence of SEQ ID No. 1 or an amino acid sequence which comprises deletion, substitution, and/or insertion of one or more amino acid residues at the positions 1, 3, 6, 13, 14 and/or 15 of SEQ ID No.1.

2. The peptide of claim 1, which specifically inhibits ADP-ribosyl cyclase activity of BST-1.

3. The peptide of claim 1, which specifically inhibits cADP-ribose hydrolase activity of BST-1.

4. A composition comprising the peptide of claim 1.

5. A diagnostic agent for detecting BST-1, which comprises the peptide of claim 1.

6. An adsorbing agent comprising the peptide of claim 1 immobilized on a carrier.

7. A method of purifying BST-1 comprising binding the adsorbing agent of claim 6 with BST-1 to purify BST-1.

8. A medical extraperfusion apparatus which comprises, as one of the components, the peptide of claim 1 inhibiting the enzymatic activity of BST-1.

9. A method of screening a peptide inhibitor of BST-1, said method comprising (a) binding the peptide of claim 1 with BST-1 in the presence of the peptide inhibitor, (b) binding said peptide with BST-1 without the presence of the peptide inhibitor and (c) comparing the binding activities of said peptide in (a) and (b) to determine whether the inhibitor inhibits BST-1 binding to the peptide of claim 1.

10. A peptide which binds to bone marrow stromal cell antigen-1, said peptide comprising an amino acid sequence of amino acid residues 1–12 of SEQ ID No. 1 or an amino acid sequence which comprises deletion, substitution and/or insertion of one or more amino acid residues at the positions 1, 3 and/or 6 of SEQ ID No. 1.

11. The peptide of claim 10, which specifically inhibits ADP-ribosyl cyclase activity of BST-1.

12. The peptide of claim 10, which specifically inhibits cADP-ribose hydrolase activity of BST-1.

* * * * *

SEQUENCE LISTING

<160> NUMBER OF SEQ ID NOS: 2

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Synthetic -continued

```
      peptide

<400> SEQUENCE: 1

His Ser Gln Ile Ser Gly Lys Tyr Gln Arg Tyr Leu Lys Asp Ala
  1               5                  10                  15

<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Asp Asp Val Val Tyr Thr Asn Ile His Lys Trp Gly Arg Arg Glu
  1               5                  10                  15
```